(12) United States Patent
Liu et al.

(10) Patent No.: US 9,731,066 B2
(45) Date of Patent: Aug. 15, 2017

(54) DEVICE, SYSTEM AND METHOD OF AUTOMATIC VESSEL ACCESS BASED ON REAL TIME VOLUMETRIC ULTRASOUND

(71) Applicant: General Electric Company, Schenectady, NY (US)

(72) Inventors: Gang Liu, Liaoning (CN); You Chen, Jiangsu (CN); Liping Chen, Jiangsu (CN); Shuxiu Wang, Jiangsu (CN)

(73) Assignee: General Electric Company, Schenectady, NY (US)

( * ) Notice: Subject to any disclaimer, the term of this patent is extended or adjusted under 35 U.S.C. 154(b) by 1213 days.

(21) Appl. No.: 13/630,710

(22) Filed: Sep. 28, 2012

(65) Prior Publication Data

US 2013/0090600 A1    Apr. 11, 2013

(30) Foreign Application Priority Data

Sep. 30, 2011    (CN) .......................... 2011 1 0312383

(51) Int. Cl.
*A61M 5/00* (2006.01)
*A61B 8/08* (2006.01)
(Continued)

(52) U.S. Cl.
CPC ............... *A61M 5/00* (2013.01); *A61B 8/085* (2013.01); *A61B 8/0841* (2013.01); *A61B 8/483* (2013.01); *A61B 90/37* (2016.02); *A61B 2017/3405* (2013.01); *A61B 2017/3409* (2013.01); *A61B 2017/3413* (2013.01);
(Continued)

(58) Field of Classification Search
CPC ...................................................... A61B 8/483
See application file for complete search history.

(56) References Cited

U.S. PATENT DOCUMENTS 5,415,177 A    5/1995  Zadini
6,068,599 A    5/2000  Saito et al.
(Continued)

FOREIGN PATENT DOCUMENTS

CN           1636520 A      7/2005
CN        101175520 A       5/2006
(Continued)

OTHER PUBLICATIONS

Unofficial English translation of Chinese Office Action and Search Report issued in connection with corresponding CN Application No. 201110312383.2 on Jan. 4, 2016.
(Continued)

*Primary Examiner* — Joseph M Santos Rodriguez (57) ABSTRACT

An automatic vessel access device based on real time volumetric ultrasound is provided. The automatic vessel access device comprises a probe configured to generate a VOI image of a candidate vessel in a real time volume ultrasound scan mode, a control device coupled to the probe, and at least one motor coupled to the control device. The control device comprises at least one processing module configured to determine at least one control parameter based on the VOI image, and a driver module coupled with the at least one processing module and configured to drive the at least one motor to automatically access the candidate vessel according to the at least one control parameter.

18 Claims, 7 Drawing Sheets

(51) Int. Cl.
*A61B 90/00* (2016.01)
*A61M 25/09* (2006.01)
*A61M 25/01* (2006.01)
*A61B 17/34* (2006.01)

(52) U.S. Cl.
CPC .. *A61B 2090/378* (2016.02); *A61M 25/09041* (2013.01); *A61M 2025/0166* (2013.01)

(56) References Cited

U.S. PATENT DOCUMENTS

| | | |
|---|---|---|
| 6,361,499 B1 | 3/2002 | Bates et al. |
| 6,695,786 B2 | 2/2004 | Wang et al. |
| 8,123,691 B2 | 2/2012 | Mine et al. |
| 2005/0182295 A1 | 8/2005 | Soper et al. |
| 2008/0195043 A1 | 8/2008 | Schwach et al. |
| 2008/0221519 A1 | 9/2008 | Schwach et al. |
| 2009/0275823 A1 | 11/2009 | Ayati et al. |
| 2010/0177177 A1 | 7/2010 | Sonnemans et al. |
| 2010/0210934 A1 | 8/2010 | Belson |
| 2010/0312109 A1* | 12/2010 | Satoh ............. A61B 8/06 600/441 |
| 2011/0166451 A1 | 7/2011 | Blaivas et al. |

FOREIGN PATENT DOCUMENTS

| | | |
|---|---|---|
| CN | 101076284 A | 11/2007 |
| CN | 101193595 A | 6/2008 |
| CN | 101681514 A | 3/2010 |
| EP | 1348377 A1 | 10/2003 |
| JP | 6216744 A | 1/1987 |
| JP | 08138077 A | 5/1996 |
| JP | 2002102221 A | 4/2002 |
| JP | 2005058584 A | 3/2005 |
| WO | 2006111939 A2 | 10/2006 |
| WO | 2006120619 A2 | 11/2006 |

OTHER PUBLICATIONS

Office Action issued in connection with orresponding CN Application No. 201110312383.2 dated on Jun. 22, 2016.

Japanese Search Report issued in connection with corresponding JP Application No. 2012-209038 dated Jul. 29, 2016.

Office Action issued in connection with corresponding JP Application No. 2012209038 dated on Sep. 6, 2016.

* cited by examiner

DEVICE, SYSTEM AND METHOD OF AUTOMATIC VESSEL ACCESS BASED ON REAL TIME VOLUMETRIC ULTRASOUND

CROSS-REFERENCE TO RELATED APPLICATIONS

This application claims foreign priority benefits under 35 U.S.C. §119 to co-pending Chinese Patent Application No. 201110312383.2, filed Sep. 30, 2011, which is hereby incorporated by reference in its entirety as part of the present disclosure.

BACKGROUND OF THE INVENTION

Embodiments of the present invention generally relate to a device, a system and a method of automatic vessel access and, more particularly, to a device, a system and a method of automatic vessel access based on real time volumetric ultrasound.

Currently, blood vessel access of neonatology (for example: PIV, PAC, PICC, etc.) is generally accomplished by manual operation. However, blood vessel access of neonatology based on manual operation is difficult for the operator of vessel access because babies are so thin and weak that the operators need to have sufficient clinical experience to observe their vessels and perform manual vessel access. Moreover, this difficulty also exists for adults whose vessels are not very obvious.

U.S. Pat. No. 5,415,177, filed on Dec. 31, 1992 and issued on May 16, 1995, discloses a guide wire placement device. The device comprises a self-propelled device which can make the guide wire inside the cavity of the needle move into the candidate's vessel intravascular automatically upon the operator's manual penetration of the wall of a blood vessel by the needle.

U.S. patent application Ser. No. 11/009,699 (Publication No. US2005/0182295 A1), filed on Dec. 10, 2004 and published on Aug. 18, 2005, discloses a visual assisted guidance device used to guide an endoscope to arrive a predetermined volume of interest within a lung during a Bronchoscope procedure, wherein non-invasive imaging technology such as HRCT is applied.

U.S. patent application Ser. No. 12/598,053 (Publication No. US2010/0210934 A1), filed on May 7, 2008 and published on Aug. 19, 2010, discloses a method and a device to place an intravenous catheter using guide wire assistance, which is used in the catheter insertion and blood collection fields.

Although the teaching of the above patents or patent applications provide certain assisted features and inspirations for vessel access operation, the operators have to see the vessel and guarantee that a needle is inserted manually into the vessel wall before automatically moving a guide wire to an advanced position. This is still a challenge to vessel access of neonates.

BRIEF SUMMARY OF THE INVENTION

According to an embodiment of the present invention, an automatic vessel access device based on real time volumetric ultrasound is provided. The automatic vessel access device comprises a probe configured to generate a VOI image of a candidate vessel in a real time volume ultrasound scan mode, a control device coupled to the probe, and at least one motor coupled to the control device. The control device comprises at least one processing module configured to determine at least one control parameter based on the VOI image, and a driver module coupled with the at least one processing module and configured to drive the at least one motor to automatically access the candidate vessel according to the at least one control parameter.

According to an embodiment of the present invention, an automatic vessel access device based on real time volumetric ultrasound is provided. The automatic vessel access device comprises a probe coupled to an ultrasound scanner module, wherein the ultrasound scanner module is configured to generate a VOI image of a candidate vessel in a real time volumetric ultrasound scan mode by using the probe, a control module coupled with the ultrasound scanner module and comprising at least one processing module configured to determine at least one control parameter according to the VOI image, and a motor driver module coupled with the control module and configured to drive the operation of at least one motor to automatically access the candidate vessel according to the at least one control parameter.

According to an embodiment of the present invention, an automatic vessel access method based on real time volumetric ultrasound is provided. The method comprises setting a probe to a real time volumetric ultrasound scan mode, generating a VOI image of a candidate vessel by using the probe, determining at least one control parameter according to the VOI image; and using the at least one control parameter to automatically control vessel access.

BRIEF DESCRIPTION OF THE DRAWINGS

These and other features, aspects and advantage of the embodiments of the present invention can be better understood when the following detailed description is read with reference to the accompanying drawings, in which.

DETAILED DESCRIPTION OF THE INVENTION

According to embodiments of the present invention, an operator can accurately insert a needle without seeing the vessel, i.e. automatically (for example, fully-automatically or semi-automatically) accomplish different types of vessel access procedures such as PIV, PAC and PICC.

After determining an appropriate candidate vessel by using any well-known or new vessel selecting method, embodiments of the present invention provide a device, a system and a method of automatic vessel access based on real time volumetric ultrasound to automatically control the needle to insert into the candidate vessel, thus, to automatically accomplish a vessel access operation.

According to an embodiment of the present invention, an automatic vessel access device based on real time volumetric ultrasound is provided. The device comprises a probe configured to generate a VOI image of a candidate vessel in real time volumetric ultrasound scan mode, a control device coupled to the probe including at least one processing module used to determine at least one control parameter according to the VOI image, and at least one motor coupled to the control device to accomplish the automatic vessel access, wherein, the control device further comprises a driver module coupled to the at least one processing module, which is configured to drive operation of the at least one motor according to the at least one control parameter.

According to an embodiment of the present invention, an automatic vessel access system based on real time volumetric ultrasound is provided. The system comprises an ultrasound scanner module configured to use the probe coupled to it to generate a VOI image of a candidate vessel in a real time volumetric ultrasound scan mode, a control module coupled to the ultrasound scanner module comprising at least one processing module used to determine at least one control parameter according to the VOI image, and a motor driver module coupled to the control module configured to drive the operation of the at least one motor to accomplish the automatic vessel access according to the at least one control parameter.

According to an embodiment of the present invention, an automatic vessel access method based on real time volumetric ultrasound is provided. The method comprises setting a probe to a real time volumetric ultrasound scan mode, generating a VOI image of a candidate vessel by using the probe, determining at least one control parameter according to the VOI image, and automatically controlling vessel access using the at least one control parameter.

The term vessel access in this disclosure includes, but is not limited to, intravenous injection, arterial injection, and any procedure of placing material or a device into a vessel. Moreover, the term 'automatic in this disclosure includes both fully-automatic (i.e. almost no manual intervene exists) and semi-automatic (i.e. certain manual intervene exists). That is, when automatic is used alone in this disclosure, it means that there could be certain extents of manual intervention or no manual intervention during a vessel access procedure. Furthermore, the term needle in this disclosure includes, but is not limited to, an injection needle, a hollow needle with devices such as catheter, and any object that is appropriate to insert through human tissue for accomplishing vessel access.

Figure 1:
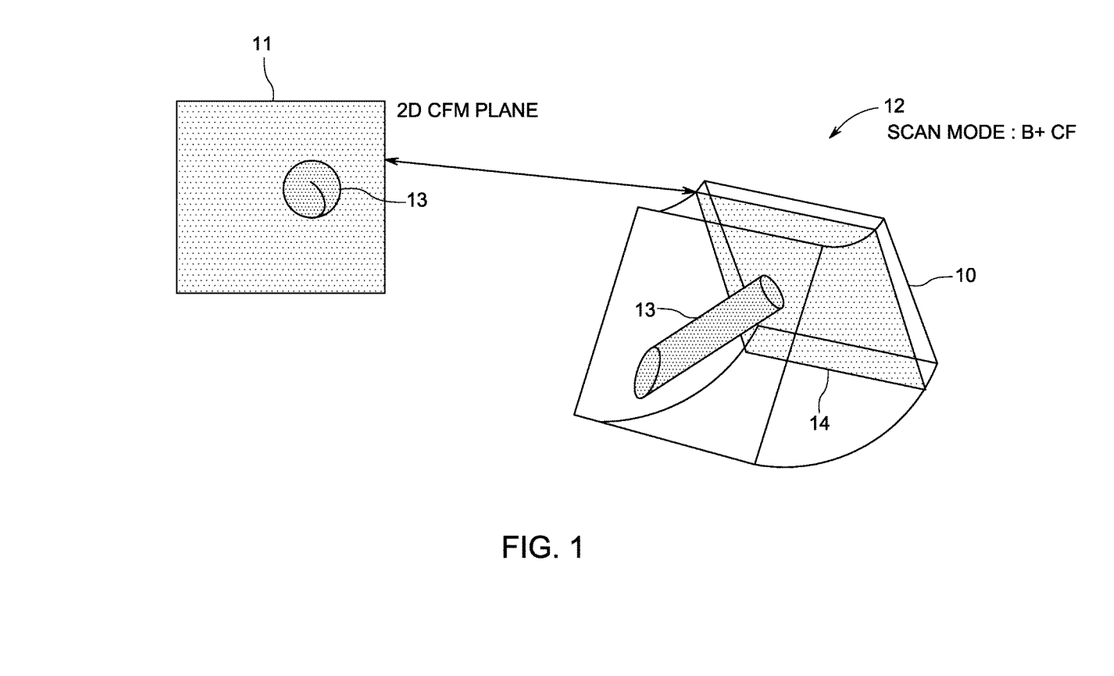
FIG. 1 is a schematic diagram of setting up a real time volumetric scan mode according to an embodiment of the present invention.

FIG. 1 shows how to perform a real time volumetric scan. The right side of FIG. 1 shows a schematic probe 10 and the schematic result of using probe 10 in ultrasound scan CF (Color Blood Flow) mode and B mode to perform the real time volumetric scan. Particularly, at each given moment, the real time volumetric scan is performed on a target vessel 13 (for example, vessel of baby's arm) through probe 10 in B mode or CF mode, wherein the scan direction of probe 10 may be substantially parallel with that of the long-axis of the vessel 13. In an embodiment, most parts of the scan coverage of probe 10 are scanned in B mode, resulting in a group of gray scale images for displaying images of the vessel 13 and/or the needle (which will be described in more details below). Moreover, scanning in CF mode (CFM) is only performed around the largest scan angle of probe 10, with the resultant color image being used to display information about the blood flow in vessels (for example, blue means flow away from the probe, and red means flow towards the probe), and then the type of vessel (for example, artery, vein, etc.) can be determined.

The left side of FIG. 1 shows a 2-Dimension (2D) CFM plane projection 11 according to an embodiment of the present invention. The plane projection 11 is formed by capturing the image from the real time volumetric scan in CF mode via probe 10 in FIG. 1 at a plane 14, which will be described in more detail below with reference to FIGS. 2A-2B. Since the vessel 13 shown in the middle of the projection 11 is colored (for example, red or blue), the type of vessel can be determined according to the color. The volume of interest (VOI) can be defined by determining the position and the thickness of a vessel 13 through analysis and calculation on the plane projection 11. Only the scan data within VOI is meaningful. In an embodiment, only the data within VOI is stored and displayed.

Figure 2A:
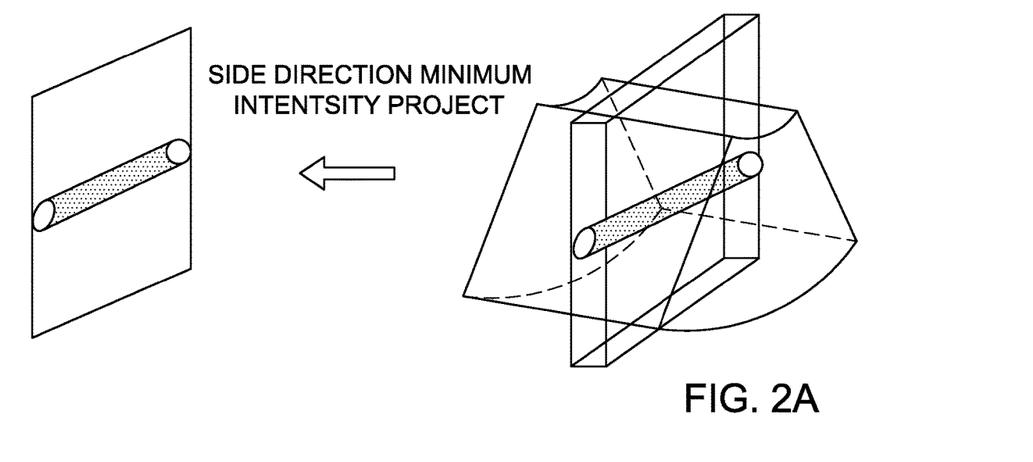
FIG. 2A shows an exemplary procedure of generating a side view image of vessel according to an embodiment of the present invention.
Figure 2B:
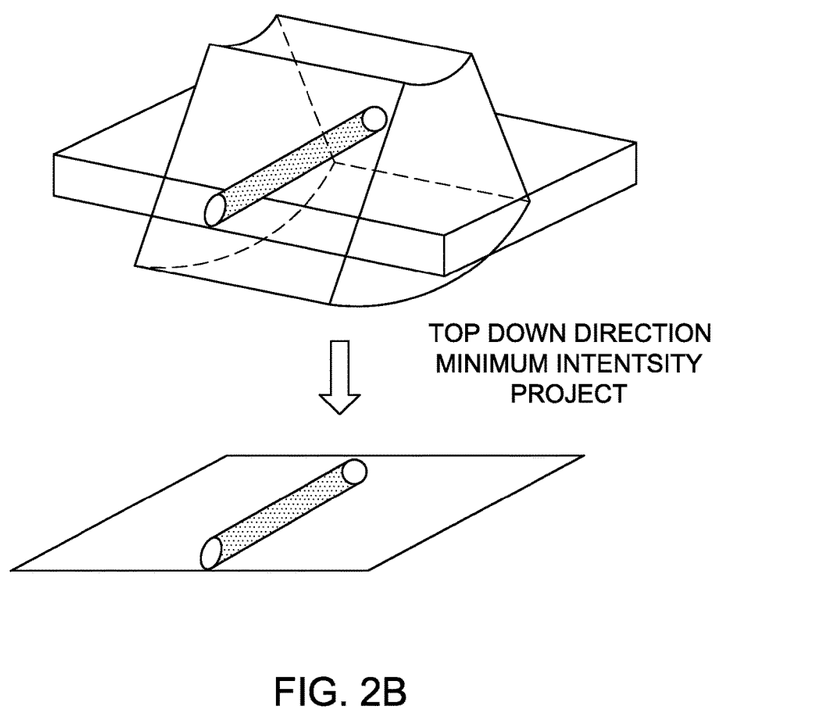
FIG. 2B shows an exemplary procedure of generating a top view image of vessel according to an embodiment of the present invention.

Next is a brief description of how to project VOI containing vessel image into 2D plane projection with reference to FIGS. 2A-2B. FIG. 2A shows the procedure for forming a side view of a vessel by projecting the determined VOI to the left side, wherein minimum intensity projection in the side direction is applied. FIG. 2B shows the procedure for forming a top view of a vessel by projecting the determined VOI from top to down, wherein minimum intensity projection from top to down direction is applied.

The above description uses B mode and CF mode of real time volumetric ultrasound scan as an example to illustrate the exemplary procedure to obtain the top view image and side view image of a desired vessel by using the probe. However, those skilled in the art should appreciate that the above description is only exemplary, and various improvements and modifications can be made on the selection of scan modes, the determination of vessel types, the concrete projection types, etc., without departure from the scope of the present invention.

Figure 3:
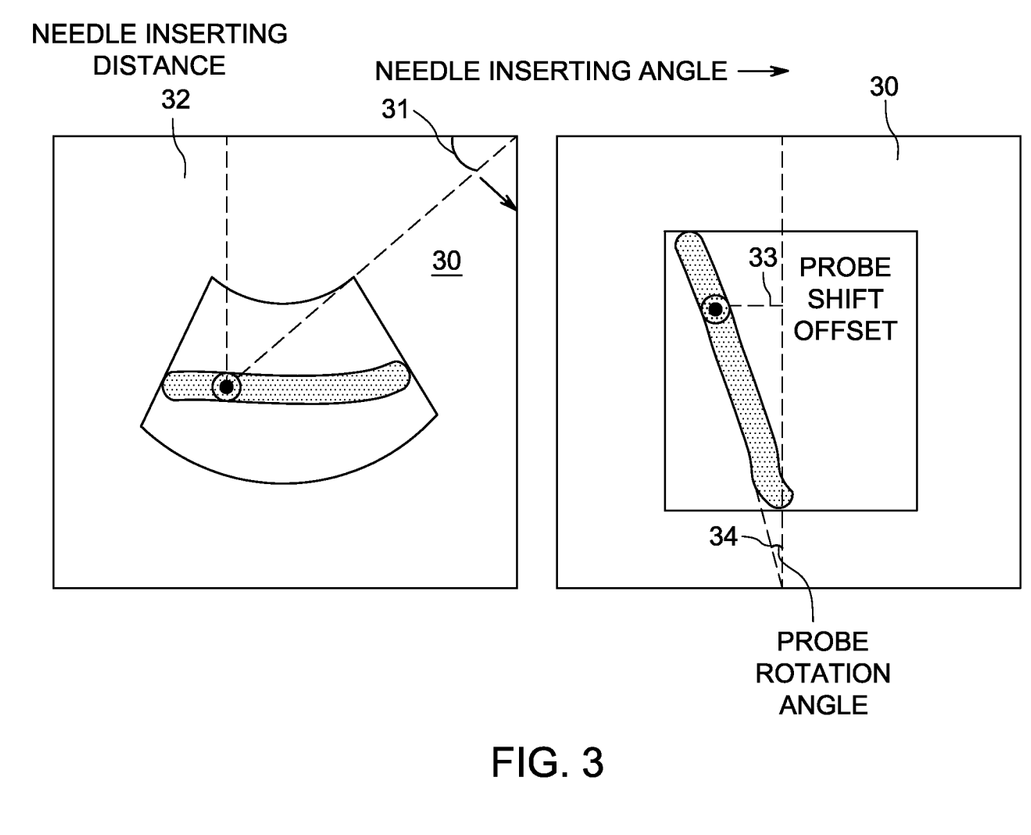
FIG. 3 shows a schematic diagram of calculating the device control parameters for vessel access by using a vessel position according to an embodiment of the present invention.

FIG. 3 shows a schematic diagram of calculating device control parameters for vessel access based on a vessel side view and a vessel top view displaying the vessel position respectively according to an embodiment of the present invention. In each view of FIG. 3, thick dash line 30 represents the needle guide wire when performing vessel access, wherein the guide wire should be followed when a needle or a needle head (shown in FIG. 4) is inserted into the vessel, and wherein the concentric circles in the vessel represent the reference position for needle insertion. More particularly, the vessel side view shown on the left of FIG. 3 shows how to determine the parameters associated with the needle, such as the needle inserting angle 31 and the needle inserting distance 32. The vessel top view shown on the right of FIG. 3 shows how to determine the parameters associated with the probe, such as the probe shift offset 33 and the probe rotation angle 34. The probe rotation angle 34 is chosen, as shown, to control the probe, thus making the vessel in the real time volumetric ultrasound image output by the probe parallel with the guide wire 30. The probe shift offset 33 is chosen to guarantee that the guide wire 30 is in the middle of the vessel in the vessel image output by the probe, wherein the probe is moved by the probe shift offset

33. On the other hand, the needle inserting angle 31 is chosen as shown to control the needle to rotate (shown in FIG. 4) to a desired inserting angle; and the needle inserting distance 32 controls the movement of the needle so that a desired inserting distance can be reached. Those skilled in the art could appreciate that the chosen parameters associated with the needle and the chosen parameters associated with the probe are only exemplary, or varied parameters associated with the needle and/or parameters associated with the probe can be chosen according to an actual demand, as long as these parameters can control the corresponding probe/needle to the desired position when used together or separately. For example, when one end of the probe is fixed directly over the target to be detected (for example, a baby's arm), it is possible to choose only the probe rotation angle as the control parameter of the probe.

Figure 4:
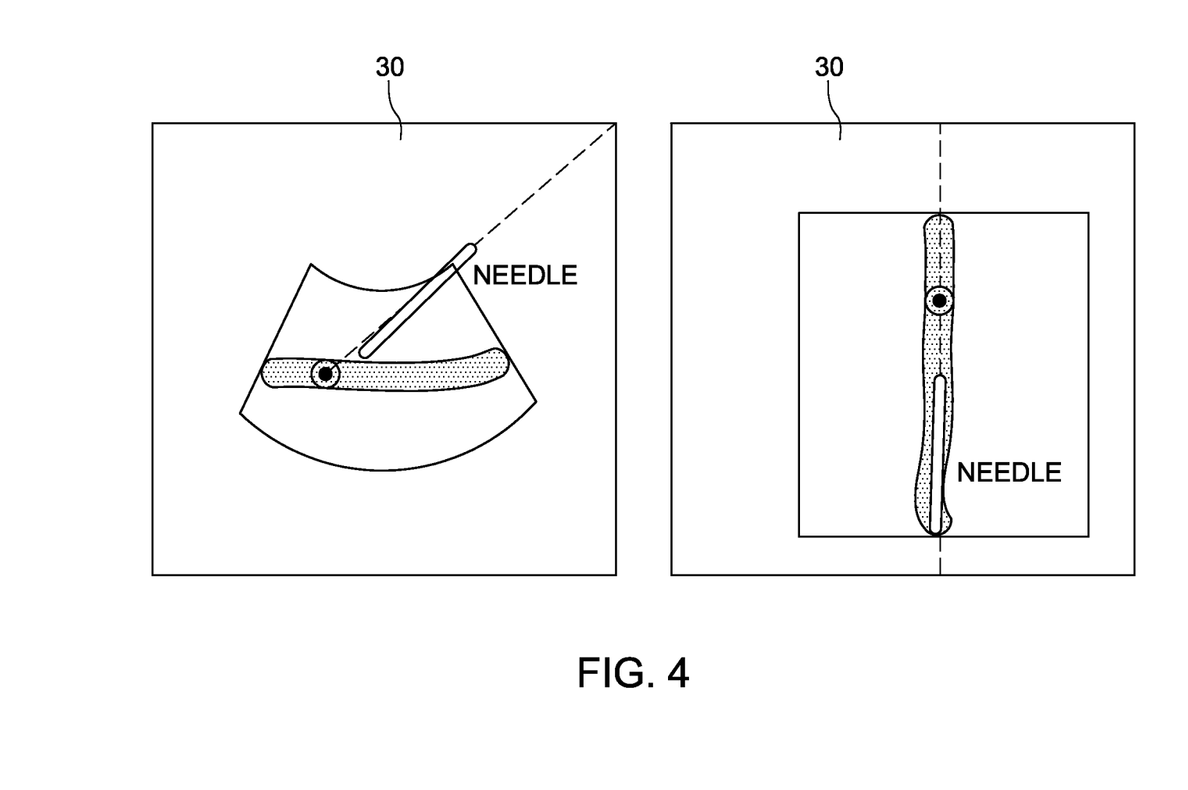
FIG. 4 shows a schematic diagram of a vessel image with a needle inserted according to an embodiment of the present invention, wherein a vessel access procedure is at least partially adjusted according to the parameters calculated in FIG. 3.

FIG. 4 shows a vessel side view and a vessel top view with a needle inserted according to an embodiment of the present invention. The 2D vessel top view on the right of FIG. 4 shows that the guide wire 30 (and the needle inserting along the guide wire 30) is in the middle of the vessel in the 2D vessel top view output from the probe since the probe has been adjusted according to the parameters associated with the probe calculated in FIG. 3. Meanwhile, the vessel side view on the left of FIG. 4 shows the relative position between the vessel and the needle which is inserted along the guide wire 30. In an embodiment, the vessel top view and the vessel side view containing the needle are displayed and stored at the same time.

An embodiment of the automatic vessel access procedure based on real time volumetric ultrasound is described above with reference to FIGS. 3-4, in which the positions of the probe and the needle are adjusted according to the control parameters in the VOI image, so as to achieve the purpose of accurate vessel access. Examples of automatic vessel access systems and devices according to embodiments of the present invention are described below with reference to FIGS. 5-7.

Figure 5:
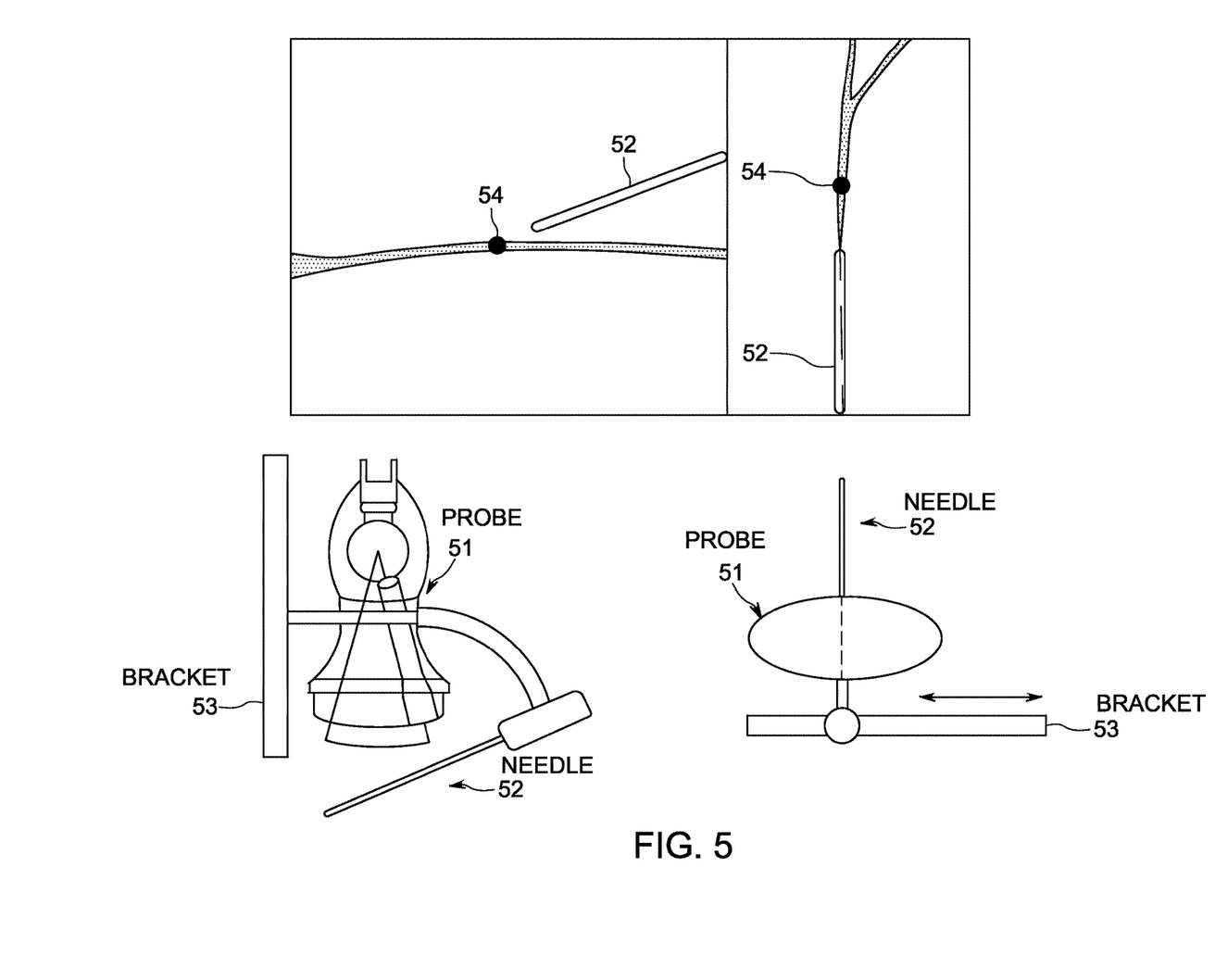
FIG. 5 is a schematic diagram of a semi-automatic vessel access device which achieves semi-automatic vessel access by using a real time vessel access image according to an embodiment of the present invention.

FIG. 5 is a schematic diagram of a semi-automatic vessel access device which achieves semi-automatic vessel access by using the real time vessel access image according to an embodiment of the present invention. The upper part of FIG. 5 shows the side view (left side) and the top view (right side) of the vessel scan image output by using a probe 51, wherein the needle 52 is inserted towards the vessel along the predetermined guide wire; and the bottom part of FIG. 5 shows the side view (left side) and top view (right side) of the probe 51 and a needle 52 placed on a bracket 53.

In an embodiment of the present invention, one can use the semi-automatic vessel access device in FIG. 5 to perform the operation of semi-automatic vessel access. More particularly, an operator first adjusts (for example, rotates or shifts) the position of probe 51 according to the real time vessel top view so as to guarantee that the guide wire is in the middle of the vessel in the real time vessel top view output by the adjusted probe 51, as shown in the view at the top right of FIG. 5. Then, the operator adjusts and inserts the needle 52 according to the real time vessel side view output by the probe 51 so as to guarantee that the needle can be inserted to a desired position along the guide wire 30. The view at the top left of FIG. 5 shows a schematic diagram when the needle is inserted for a certain distance along the guide wire 30, and the dot 54 shown in the schematic diagram represents where the needle will finally be inserted into the vessel.

The procedure of how to accomplish semi-automatic vessel access with the intervention of an operator is described above with reference to the device of FIG. 5. Those skilled in the art will understand that the methodology of the access described above is only exemplary, and that several access steps can be adjusted, added and deleted as desired. For example, a positioning device such as a stepper motor (not shown) can be used to control the position of probe 51 according to probe shift offset 33 and probe rotation angle 34 (shown in FIG. 3), thus adjusting the position of probe 51 by an operator according to the real time vessel top view can be skipped to get a faster and more precise probe positioning. Under such circumstances, the real time vessel top view may not be displayed. Furthermore, the executable code which implements the function above (for example, a computer program) and the real time vessel top view, can be stored in a memory (not shown), and the memory can be coupled with any proper control system for controlling the positioning device. The control system uses the executable code in the memory and the stored real time vessel top view, if needed, to calculate and adjust the probe to the desired position according to the probe shift offset and probe rotation angle. The memory may include, but is not limited to, ROM memory, RAM memory, etc. Other similar variations are obvious for those skilled in the art.

Figure 6:
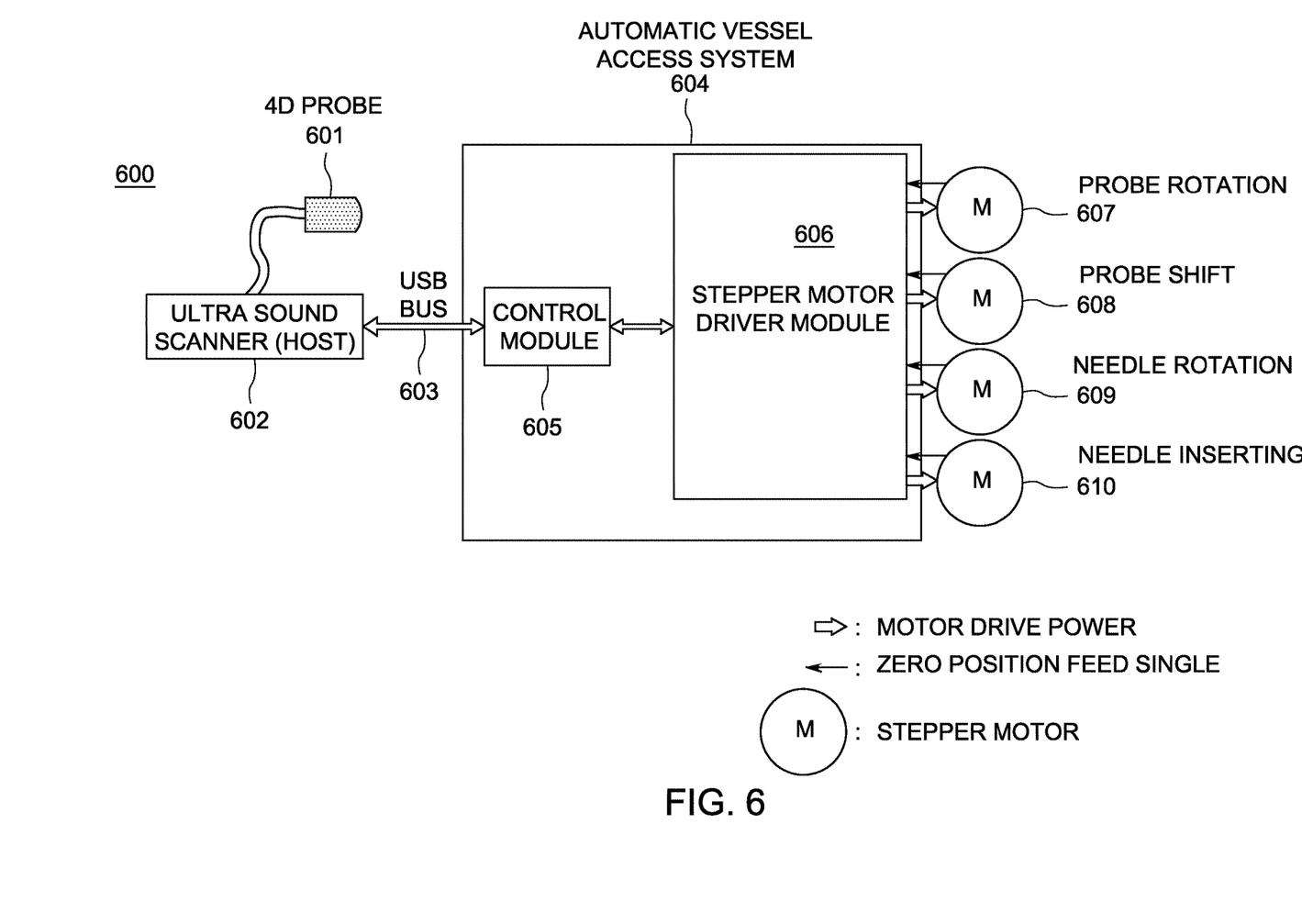
FIG. 6 is a function diagram of a fully-automatic vessel access system which achieves fully-automatic vessel access by using a real time vessel access image according to an embodiment of the present invention.

Comparing FIG. 6 to FIG. 5, FIG. 6 is a function block diagram 600 of a fully-automatic vessel access system which achieves fully-automatic vessel access by using a real time vessel access image according to an embodiment of the present invention. The fully-automatic vessel access system, as shown in FIG. 6, comprises a host 602 equipped with a 4D probe 601 and is used to generate real time ultrasound scan image, wherein the host 602 is coupled to an automatic vessel access system 604 through a link such as a USB bus 603 and transmits the real time ultrasound scan image to the automatic vessel access system 604. More particularly, a control module 605 of the automatic vessel access system 604 receives the real time ultrasound scan image from the USB bus 603 through an interface device (not shown), and calculates the ultrasound scan image by a processing module (not shown, including but not limited to DSP, MCU, CPU, etc.) of the control module 605 to obtain parameters associated with the needle and parameters associated with the probe 601 (generally referred as parameters). Those skilled in the art will understand that receiving through the interface device may further comprise performing signal processing, such as analog digital conversion, filtering, etc., on the real time ultrasound scan image, so as to obtain the data that is suitable for the control module 605 to recognize and for further process. According to an embodiment of the present invention, VOI can be transmitted only through USB bus 603 so as to save transmission bandwidth.

According to an embodiment of the present invention, the control module 605 further includes a selection module, which can be used to configure the ultrasound module 602 according to instructions input by a user (for example, through an input device (not shown) coupled to the control module 605), so that the ultrasound module 602 will perform volumetric ultrasound scans in B mode and/or CF mode. Moreover, the concrete types, calculation methodologies of the above control parameters have been described in detail with reference to FIG. 3, and thus will not be repeated.

After a processing module in the control module 605 calculates the corresponding control parameters, a motor driver module coupled to the control module 605 (for example, stepper motor driver module 606) will control the corresponding motor according to the above control parameters, thus controlling the spatial position and inserting depth, etc. of the probe 601 and the needle (not shown). In an embodiment, the stepper motor driver module 606 is integrated within the automatic vessel access system 604, but it can be also a separate device. In an embodiment of the present invention, the stepper motor driver module 606 drives four stepper motors, so as to control a probe rotation 607, a probe shift 608, a needle rotation 609 and a needle inserting 610 respectively.

Figure 7:
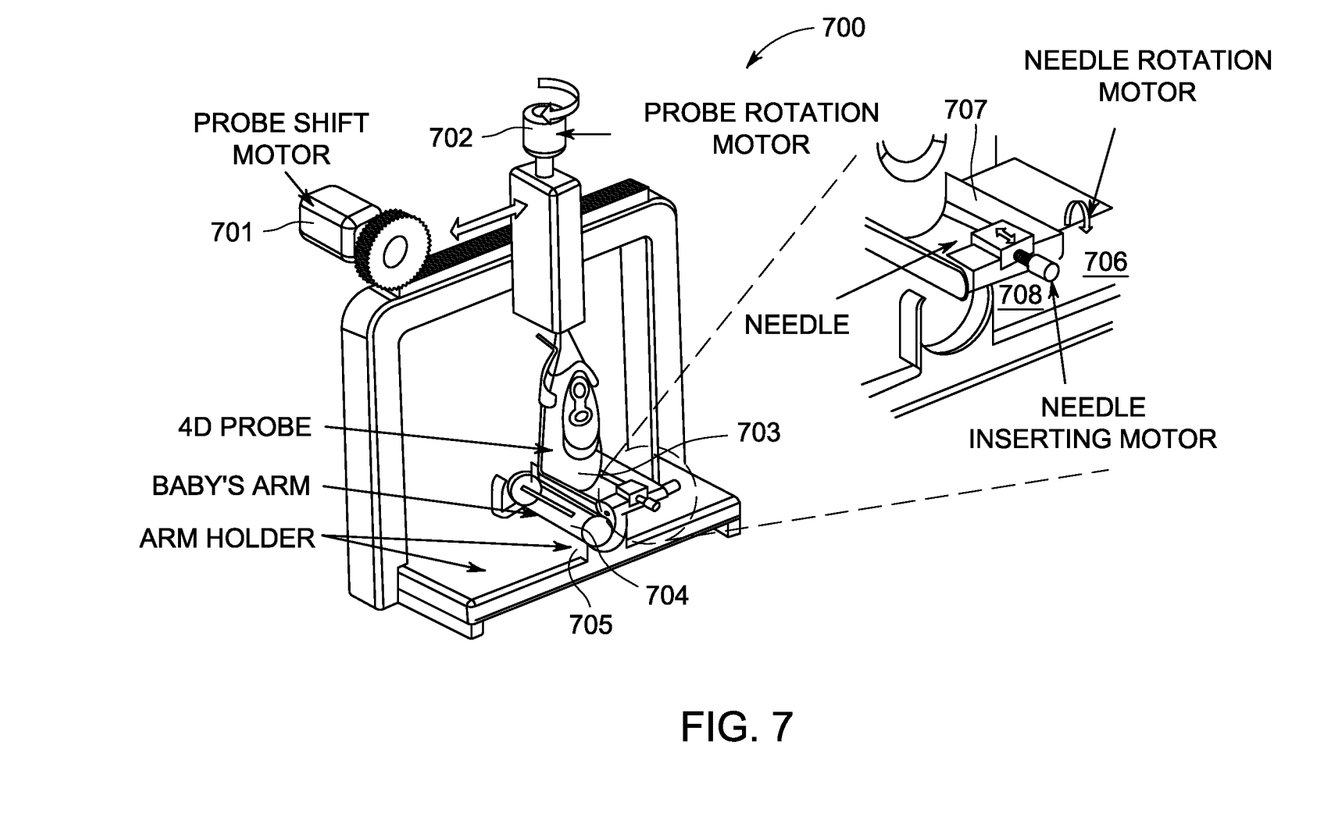
FIG. 7 shows a schematic diagram of a fully-automatic vessel access device according to an embodiment of the present invention.

FIG. 7 schematically shows a fully-automatic vessel access device 700 according to an embodiment of the present invention. Fully-automatic vessel access device 700 comprises a probe 703 configured to generate a real time ultrasound scan image of the candidate vessel (preferably VOI image) in a real time volumetric ultrasound scan mode, a control device (not shown) coupled with probe 703, which includes multiple processing modules used to determine multiple control parameters for fully-automatic vessel access according to the real time ultrasound scan image, and multiple motors coupled with the control device, which perform fully-automatic vessel access under the control of the control device.

In the embodiment described with reference to FIG. 7, the numbers of the processing modules and the motors are both four, and there is one-to-one correspondence between them. Four processing modules calculate four control parameters, i.e. a probe rotation angle, a probe shift offset, a needle insertion angle, and a needle inserting distance. More particularly, the four processing modules are coupled to and control the corresponding motors respectively the processing module for calculating the probe rotation angle being coupled to and controls the probe rotation motor 702 for controlling the rotation of the probe, the processing module for calculating the probe shift offset being coupled to and controls the probe shift motor 701 for controlling the shift of the probe, the processing module for calculating the needle insertion angle being coupled to and controls the needle rotation motor 706 for controlling the rotation of the needle, and the processing module for calculating the needle inserting distance being coupled to and controls the needle inserting motor 708 for controlling the inserting of the needle.

An implementation of the fully-automatic vessel access procedure according to an embodiment of the present invention is described below with reference to the schematic diagram of fully-automatic vessel access device 700 shown in FIG. 7. First, the operations of the probe shift motor 701 and the probe rotation motor 702 are controlled by using the parameters associated with the probe (the calculation methodology is described with reference to FIG. 3, and in an embodiment, respectively by the four processing modules as described above), so that the 4D probe 703 is located relative to the baby's arm 704 placed on the arm holder 705 (the detailed requirements of the location is as described with reference with FIGS. 3-4). Then, according to the real time volumetric ultrasound image output from the 4D probe 703 successfully located, the control device (not shown) gets the parameters associated with the needle (for example, including the needle insertion angle 31 and the needle inserting distance 32). Next, as shown in the enlarged view on the right side of FIG. 7, the needle rotation motor 706 is controlled by the needle insertion angle 31, so that the needle 707 is rotated to coincide with the needle guide wire 30. Finally, the needle inserting motor 708 is controlled with the needle inserting distance 32, so that the needle 707 can finally be inserted to the desired position.

Those skilled in the art will understand that the automatic vessel access procedures described above, and other procedures, can be stored in advance in a memory (not shown) coupled with a control device in the form of executable code that can be recognized and processed by the control device (for example, computer program), so that the automatic vessel access procedure can be accomplished by invoking executable code in the memory through the control device when needed. The memory may include, but is not limited to, ROM memory, RAM memory, etc.

The fully-automatic vessel access device 700 in FIG. 7 can be made of materials containing metal or can be substantially made of plastic. According to an embodiment of the present invention, the motors for rotation (i.e. the probe rotation motor 702 and the needle rotation motor 706) are 200 steps/cycle stepper motors so as to acquire a control precision less than 2 degrees; and the motors for shift and inserting (i.e. the probe shift motor 701 and the needle inserting motor 708) are 50 steps/cycle stepper motors so as to acquire a control precision less than 0.2 mm. It shall be understood that the above selections of materials and motors are only exemplary and the motors are not limited to stepper motors. Those skilled in the art can make multiple modifications to the fully-automatic vessel access device 700 as needed, without departure from the spirit and scope of the present invention.

Moreover, according to an embodiment of the present invention, modifications can be made to the fully-automatic vessel access device 700 to form a semi-automatic vessel access device (not shown). For example, the probe shift motor 701 and the probe rotation motor 702 can be removed from the fully-automatic vessel access device 700 and a monitor (not shown) for displaying a vessel real time top view can be added, so that the operator can adjust the probe 703 to a desired position relative to the baby's arm 704 according to the display on the monitor. Similarly, the needle rotation motor 706 and the needle inserting motor 708 can be removed from the fully-automatic vessel access device 700, and a monitor (not shown) for displaying a vessel real time side view can be added, so that the operator can insert the needle 707 accurately into the candidate vessel of the baby's arm 704 according to the display on the monitor.

Embodiments of the present invention replace manual operation with automatic operation. Thus, a vessel access procedure can be accomplished with or without manual monitoring by using the device, system and method according to embodiments of the present invention. Usage of the device, system and method according to embodiments of the present invention can make a needle insertion path more accurate and steady, thus improving vessel access procedure success rate. In other words, embodiments of the present invention can reduce time consumption of vessel access, decrease the pain of the patients subject to vessel access, and lower the burden on the vessel access operators.

Moreover, since the device, system and method of automatic vessel access based on real time volumetric ultrasound according to embodiments of the present invention support fully-automatic vessel access, it is useful under circumstances when medical personal are scarce, for example, when a disaster happens.

Furthermore, the automatic vessel access devices according to embodiments of the present invention use commercially available common motors, thus the cost of manufacturing of the devices is low.

This written description uses examples to disclose embodiments of the present invention, including the best mode, and also to enable any person skilled in the art to practice the present invention, including making and using any devices or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An automatic vessel access device based on real time volumetric ultrasound, the automatic vessel access device-comprising:
   a probe configured to generate a VOI image of a candidate vessel in a real time volume ultrasound scan mode;
   a control device in communication with the probe; and
   at least one motor in communication with the control device,
   the control device comprising at least one processing module configured to determine at least one control parameter based on the VOI image, and a driver module in communication with the at least one processing module and configured to operate the at least one motor according to the at least one control parameter,
   wherein the VOI image includes a side view and a top view of a volume of interest of the candidate vessel, and the side view and the top view are acquired by using minimum intensity projection; and the processing module determines a needle insertion angle and a needle inserting distance as the control parameters based on the position of the candidate vessel in the side view, and determines a probe rotation angle and a probe shift offset as the control parameters based on the position of the candidate vessel in the top view.

2. The automatic vessel access device of claim 1, wherein the at least one motor is configured to perform at least one of: controlling the shift of the probe, controlling the rotation of the probe, controlling the rotation of the needle, and controlling the insertion of the needle, the motor being used to perform on the basis of the probe rotation angle, the probe shift offset, the needle insertion angle and the needle inserting distance determined as the control parameters.

3. The automatic vessel access device of claim 1, wherein the real time volumetric ultrasound scan mode comprises at least one of a B mode and a CF mode, and wherein the control device further comprises a selection module configured to select the corresponding real time volumetric ultrasound scan mode according to a user requirement.

4. The automatic vessel access device of claim 3, wherein the control device further comprises a determination module configured to determine the candidate vessel according to a blood flow direction.

5. The automatic vessel access device of claim 4, wherein the candidate vessel is one of a vein and an artery.

6. The automatic vessel access device of claim 1, wherein the at least one motor comprises:
   a probe shift motor configured to control the shift of the probe; and
   a probe rotation motor configured to control the rotation of the probe,
   wherein, after the probe is shifted and rotated to a desired position by the probe shift motor and the probe rotation motor, the probe calculates the parameters associated with the needle.

7. The automatic vessel access device of claim 6, wherein the at least one motor further comprises:

a needle rotation motor configured to control the rotation of the needle; and
a needle inserting motor configured to control the insertion of the needle,
wherein, after the probe is shifted and rotated to the desired position by the probe shift motor and the probe rotation motor, the needle rotation motor and the needle insertion motor are controlled according to the calculated parameters associated with the needle.

8. An automatic vessel access system based on real time volumetric ultrasound, the automatic vessel access system comprising:
   a probe in communication with an ultrasound scanner module, wherein the ultrasound scanner module is configured to generate a VOI image of a candidate vessel in a real time volumetric ultrasound scan mode by using the probe;
   a control module in communication with the ultrasound scanner module and comprising at least one processing module configured to determine at least one control parameter according to the VOI image; and
   a motor driver module in communication with the control module and configured to operate at least one motor to achieve the automatic vessel access according to the at least one control parameter,
   wherein the VOI image includes a side view and a top view of a volume of interest of the candidate vessel, and the side view and the top view are acquired by using minimum intensity projection; and the processing module determines a needle insertion angle and a needle inserting distance as the control parameters based on the position of the candidate vessel in the side view, and determines a probe rotation angle and a probe shift offset as the control parameters based on the position of the candidate vessel in the top view.

9. The automatic vessel access system of claim 8, wherein the at least one motor is configured to perform at least one of: controlling the shift of the probe, controlling the rotation of the probe, controlling the rotation of a needle, and controlling the insertion of the needle, the motor being used to perform on the basis of the probe rotation angle, the probe shift offset, the needle insertion angle and the needle inserting distance determined as the control parameters.

10. The automatic vessel access system of claim 8, wherein the real time volumetric ultrasound scan mode comprises at least one of a B mode and a CF mode, and wherein the control module further comprises a selection module configured to select the corresponding real time volumetric ultrasound scan mode according to a user requirement.

11. The automatic vessel access system of claim 10, wherein the control module further comprises a determination module configured to determine the candidate vessel according to a blood flow direction.

12. The automatic vessel access system of claim 11, wherein the candidate vessel is one of a vein and an artery.

13. The automatic vessel access system of claim 8, wherein the at least one motor comprises:
   a probe shift motor configured to control the shift of the probe; and
   a probe rotation motor configured to control the rotation of the probe,
   wherein, after the probe is shifted and rotated to a desired position by the probe shift motor and the probe rotation motor, the probe calculates the parameters associated with the needle.

14. The automatic vessel access system of claim 13, wherein the at least one motor further comprises:
   a needle rotation motor configured to control the rotation of the needle; and
   a needle insertion motor configured to control the insertion of the needle,
   wherein, after the probe is shifted and rotated to the desired position by the probe shift motor and the probe rotation motor, the needle rotation motor and the needle insertion motor are controlled according to the calculated parameters associated with needle.

15. An automatic vessel access method based on real time volumetric ultrasound, the method comprising:
   setting a probe to a real time volumetric ultrasound scan mode;
   generating a VOI image of a candidate vessel by using the probe, wherein the VOI image includes a side view and a top view of a volume of interest of the candidate vessel, and acquiring the side view and the top view by using minimum intensity projection;
   determining at least one control parameter according to the VOI image;
   using the at least one control parameter to control vessel access automatically; and
   determining a needle insertion angle and a needle inserting distance as the control parameters based on the position of the candidate vessel in the side view, and determines a probe rotation angle and a probe shift offset as the control parameters based on the position of the candidate vessel in the top view.

16. The method of claim 15, wherein the real time volumetric ultrasound scan mode comprises at least one of a B mode and a CF mode.

17. The method of claim 16, wherein the candidate vessel is determined according to a blood flow direction.

18. The method of claim 17, wherein the candidate vessel is one of a vein and an artery.

* * * * *